United States Patent [19]

Laske

[11] 4,125,985
[45] * Nov. 21, 1978

[54] PROCESS FOR FORMING PEELABLE SEALS

[75] Inventor: Louis L. Laske, Grays Lake, Ill.

[73] Assignee: Vonco Products, Inc., Lake Villa, Ill.

[*] Notice: The portion of the term of this patent subsequent to Dec. 16, 1992, has been disclaimed.

[21] Appl. No.: 833,036

[22] Filed: Sep. 14, 1977

Related U.S. Application Data

[63] Continuation-in-part of Ser. No. 641,151, Dec. 15, 1975, Pat. No. 4,055,454, which is a continuation-in-part of Ser. No. 499,621, Aug. 22, 1974, Pat. No. 3,926,311.

[51] Int. Cl.² .......................... B65B 7/02; B65B 51/10
[52] U.S. Cl. .......................................... 53/452; 53/377; 53/487; 156/290; 156/306; 156/322; 428/194; 428/296
[58] Field of Search ............... 156/290, 306, 322, 289; 264/280, 284, 324, 340, 345, 126; 428/194, 198, 296; 206/439; 53/39, 41, 29

[56] References Cited

U.S. PATENT DOCUMENTS

| 3,701,699 | 10/1972 | Jackson | 53/39 |
| 3,910,410 | 10/1975 | Shaw | 53/29 |
| 3,910,410 | 10/1975 | Shaw | 53/39 |
| 3,923,578 | 12/1975 | Hair | 156/290 |
| 3,926,311 | 12/1975 | Laske | 156/306 |
| 3,982,992 | 9/1976 | Moffitt | 156/306 |
| 4,014,433 | 3/1977 | Cerwin | 53/29 |
| 4,036,676 | 7/1977 | Pennington | 156/290 |
| 4,055,454 | 10/1977 | Laske | 156/290 |
| 4,070,222 | 1/1978 | Olson | 156/322 |

Primary Examiner—Jerome W. Massie
Attorney, Agent, or Firm—Thomas W. Speckman

[57] ABSTRACT

A process for forming peelable seals between a layer of spunbonded olefin material and an unsupported film of polyethylene or to a supported film of a laminated or coated backing, such as polyethylene coated mylar, to form a peel-seal packet, container or pouch. The spunbonded olefin material is first pretreated with a heated die in the areas that are to form the peel-seal with heat and pressure suitable to render uniform surface characteristics to the spunbonded olefin. The heat, pressure and dwell time of the pretreatment are sufficient to reduce the high spots and internal weaknesses of the spunbonded olefin material following which a web of synthetic polymeric material having a heat sealable surface may be peelably sealed by a conventional heat sealing method.

14 Claims, 3 Drawing Figures

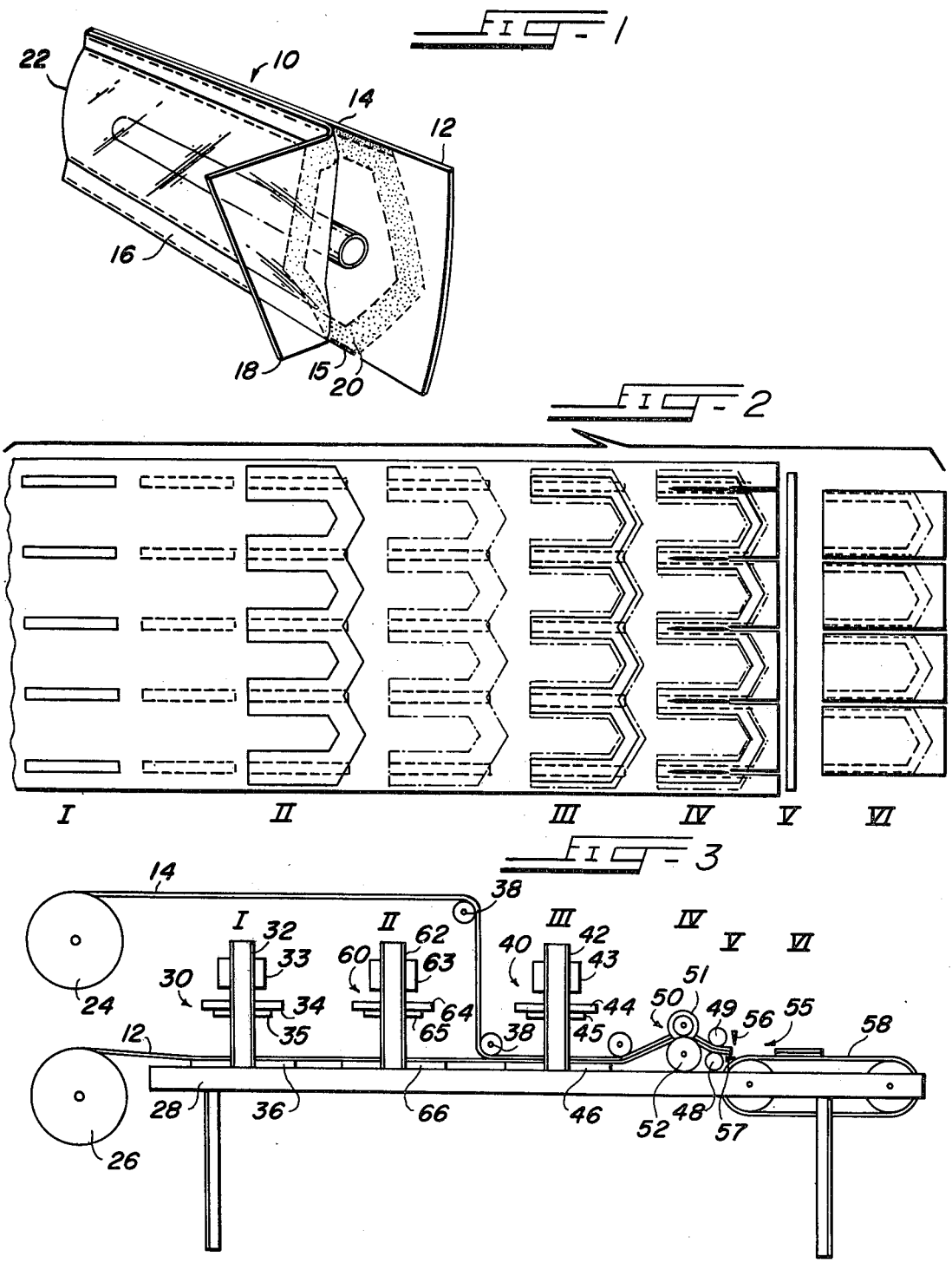

PROCESS FOR FORMING PEELABLE SEALS

CROSS REFERENCE TO RELATED APPLICATIONS

This application is a continuation-in-part of my copending application Ser. No. 641,151, filed Dec. 15, 1975, now U.S. Pat. No. 4,055,454, which is a continuation-in-part of my application Ser. No. 499,621, filed Aug. 122, 1974, now U.S. Pat. No. 3,926,311.

Spunbonded olefin sheets such as sold under the registered trademark TYVEK by DuPont, have gained use for various types of containers. Spunbonded olefin sheets are tough, durable sheets of high density polyethylene fibers. The sheets are formed by first spinning continuous strands of very fine interconnected fibers and then bonding them together with heat and pressure. The spunbonded olefin has high opacity and it is frequently desirable to have one side of the container transparent. Thus, it is desirable to produce containers with a transparent sheet such as polyethylene on one side and spunbonded olefin on the other. However, satisfactory peel-seals between the polyetheylene and spunbonded olefin have not previously been obtained, especially with the required avoidance of tearing demanded for containers of sterilized medical goods without coating the spunbonded olefin.

When it was desired to make containers using the spunbonded olefin material on one side and a transparent material such as polyethylene on the other side, experience has shown that the sealing of polyethylene directly to the spunbonded polyolefin material using conventional sealing processes has caused difficulties. Specifically, upon opening the container by peeling the polyethylene sheet from the spunbonded olefin, the spunbonded olefin material is frequently fractured internally and separated, thus providing an unsatisfactory pouch, particularly for medical uses.

Prior methods that have been used to produce peel-seal containers using spunbonded olefin have involved coating spunbonded olefin material to provide a suitable sealing surface for the polyethylene. Coating of the spunbonded olefin material has been a problem due to the uneven surface characteristics and gauge variations of the spunbonded olefin material. The coating of the spunbonded olefin, however, does reduce tearing of the spunbonded olefin when peeled from polyethylene, but increases the cost and contamination problems.

Containers have been produced sealing polyethylene to uncoated spunbonded olefin, but fabrication is very difficult, there being a very narrow range of temperature, time and pressure tolerances. Some medical and other uses permit high levels (above about five percent) of spunbonded olefin tearing upon opening as results from commercial production according to prior methods of sealing polyethylene to uncoated spunbonded olefin. It is extremely difficult if not impossible to obtain an acceptably low level (below about five percent) of spunbonded olefin tearing upon opening such containers as demanded by many medical uses or other stringent uses where tearing or loose fibers is undesirable. This is especially true when the peelable seal is desired to be formed in cases where the product is loaded before any edges of the container are sealed.

The process of this invention provides a peel-seal container or pouch which is highly reliable in providing extremely low incidence of tearing as demanded for medical uses and which can be produced at less cost than prior art methods.

The process of this invention involves a sheet of spunbonded olefin and a sheet of synthetic polymeric thermoplastic heat sealable material being fastened to each other by a peel-seal. Satisfactory polymeric thermoplastic materials include unsupported polyethylene or may be a laminate such as polyethylene laminated to polyester or a coated or laminated material having a heat sealable surface coating, such as polyethylene applied to nylon.

The process of this invention involves pretreatment of the spunbonded olefin material by applying a heated die, in the shape of at least a portion of the peel-seal desired, for a definite period of time at a pressure and temperature satisfactory to permit the direct application of a heat-sealable polymeric film to the spunbonded olefin material by conventional heat sealing techniques. The pretreatment modifies the surface of the spunbonded olefin by substantially reducing high spots and rendering the sealing area susceptible to having a synthetic polymeric material peelably joined thereto by conventional heat-pressure sealing methods. Usually it is not desirable to pretreat the whole area of spunbonded olefin since the pretreatment prevents the pouch from being breathable and thus easily sterilized. The spunbonded olefin sheet may comprise the entire side of a container or may comprise a strip or any other shape which is attached over an opening in the container material. The peel-seal need not extend entirely around the edge of the spunbonded olefin material, but only in an area sufficient to remove the product. For example, the loading end of a pouch may or may not be pretreated according to this invention depending upon whether it is necessary or desired to completely and cleanly peel off the spunbonded olefin material. Likewise, with a strip or patch of spunbonded olefin material applied to the side of a package, if it is not important to completely and cleanly remove the olefin sheet only three sides need be pretreated according to this invention, the fourth being conventionally sealed.

A container or pouch may have a peel-seal that extends to the edge of the pouch, or to the edge of the peel-seal area, or the seal may stop at a distance inward from the edge of the pouch or the edge of the spunbonded olefin sheet leaving the two sheets of material unsealed or with a weakened or relieved seal at the edges. It is preferred to pretreat the entire peel-seal area according to this invention and to provide a weakened seal at the edges to avoid unsealed areas which may become contaminated. The weakened seal may be obtained by the sealing die having a recess from the surface of about 0.002 to about 0.005 inch at the outside edges so that a weak seal is obtained at the edge. If the recess is greater than about 0.01 inch no seal would result at the edge. In cases of manufacture of multiple pouches from webs of sheet material the weakened seal may likewise be obtained by the sealing bar having a recess down the center. When the contamination is not a factor and unsealed edges are desired, a sealing die which is smaller than the outside dimensions of the spunbonded olefin sheet may be used.

Another method of providing for the peel-seal to extend to the edge of the pouch to avoid contamination and to minimize the instances of the spunbonded olefin tearing upon opening, especially where full seal strength to the edge is necessary, such as narrow seals, a second pretreatment may be applied to the edge areas with slightly higher temperatures and higher pressures.

Generally, in the manufacture of pouches according to one embodiment of this invention, the pouches are made in multiples, that is, two or more pouches across the web of plastic. In these cases, the transparent polymeric sheet is usually sealed to the spunbonded olefin sheet prior to slitting and cutting the sheets into individual pouches. Thus, it may be desirable to provide the second pretreatment to the areas which will be slit or cut after sealing when greatest resistance to tearing of the spunbonded olefin is desired.

It is also within this invention to provide only the single pretreatment to the slitting and cutting areas in cases where the prevention of tearing of the spunbonded olefin sheet is not of utmost importance.

The apparatus for use in making containers according to one embodiment of the process of this invention involves a pretreatment means for pretreatment of spunbonded olefin material in the area where the peel-seal is to be formed, which may include a first pretreatment station for treatment in the entire area of the peel-seal and a second pretreatment station for treatment at the edge and slitting and cutting areas and a sealing means where the heat-sealable polymeric film is joined in the pretreated peel-seal area to the spunbonded olefin material by conventional heat sealing techniques. Following that operation the containers may be slit and cut into the desired package, containers or pouches.

The process and containers of this invention are especially well suited for on-line loading; that is, the product to be packaged may be placed on the spunbonded olefin material after the pretreatment and the heat-sealable polymeric film sealed by conventional heat sealing techniques on all sides completely enclosing the product in one operation. It is also within this invention to place the product to be packaged on the spunbonded olefin material before the pretreatment as long as the product is not damaged by the pretreatment apparatus or temperature. It also should be apparent to one skilled in the art that the product to be packaged can be placed on the heat-sealable polymeric film and the pretreated spunbonded olefin brought into desired relationship for conventional sealing in the desired areas.

The containers made by the process of this invention provide very acceptable medical type of pouches for containing a large variety of items. The containers made according to this invention may also be used for packaging any other desired article.

The objects, advantages and features of this invention will be apparent from the description together with the drawings showing preferred embodiments, wherein:

FIG. 1 is a perspective of a partially opened container made according to the process of this invention;

FIG. 2 is a schematic top view of material as it proceeds through the apparatus of FIG. 3 to produce containers according to the process of this invention; and FIG. 3 is a side view of an apparatus to form containers according to the process of this invention.

Referring to the drawings in FIG. 1, it will be seen that container 10 results from the operation of the method of this invention utilizing the apparatus shown in FIG. 3. Container 10 comprises a sheet of spunbonded olefin material 12, such as TYVEK, a sheet of synthetic polymer material 14, for example polyethylene, a peel-seal area 16, and a peel flap 18 which provides the mechanism by which the person opening the container can grip the two layers and separate them along the area of the peel-seal.

It will be seen in FIG. 1 at the area indicated by 20 that the characteristics of the surface of spunbonded olefin of sheet 12 have been modified by pretreatment to sufficiently eliminate high spots and internal weaknesses so that utilizing conventional heat sealing techniques, sheet 14 can be sealed to the spunbonded olefin sheet to provide the peel-seal 16. The longitudinal edges have been pretreated at a higher temperature-time-pressure relationship shown as 15.

Open end 22 illustrates one way in which the container of this invention may be produced. It should be understood that the end 22 may be left open in order that the materials to be packaged can be inserted into the containers and then sealed. It is also within the scope of this invention to insert the material to be packaged prior to the time of the formation of the peel-seal so that the end 22 can be closed at the same time and in the same manner as is the remainder of the peel-seal. The seal of end 22 may be a conventional seal or a peel-seal according to the process of this invention. It is within the scope of the process of this invention to provide containers of any desired shape or any other article of sheet spunbonded olefin material in a peel-seal relationship with synthetic polymeric thermoplastic material such as polyethylene. For example, the entire side of a container may be made of the spunbonded olefin material as shown in FIG. 1 or only a portion of one side may comprise an area of spunbonded olefin sheet in peel-seal relation, such as a strip across the side, one end area, or a hole through the side material of any shape. Such areas having the peel-seal spunbonded olefin sheet covering are usually used for gaining access to the product, but it is not meant to restrict this invention only to such areas.

Referring to FIG. 3, it will be seen that roll of material 14 is provided mounted on suitable support, along with another roll 26 of spunbonded olefin material 12. Rolls 24 and 26 are mounted with suitable unwind mechanisms at the end of machine frame 28. Pretreatment station I shows pretreatment means 30 comprising base 36 having attached to it frame 32 with drive mechanism 33 and platen 34 holding die 35. The shape of the portion of die 35 which contacts the web of material 12 is the shape that is desired for the area of pretreatment. Pretreatment station II, FIG. 3, shows pretreatment means 60 comprising base 66 having attached to it frame 62 with drive mechanism 63 and platen 64 holding die 65.

In FIG. 2, the stations denoted by Roman numerals with respect to the web of plastic correspond to the stations denoted in FIG. 3. Pretreatment station I imparts the pretreatment at the slitting areas and extreme edges of the finished pouches. As explained above, the temperature-time-pressure relation is such to give increased pretreatment in the pretreatment area shown in station I than in the overall pretreatment area. A suitable die shape to obtain the desired pretreatment area is readily apparent to one skilled in the art.

As shown in FIG. 2, pretreatment station II imparts the desired pretreatment to spunbonded olefin over the entire peel-seal area. The temperature-time-pressure relation at pretreatment station II is less than that used at pretreatment station I.

While FIGS. 2 and 3 show two pretreatment stations, it should be understood that this invention encompasses the use of either pretreatment station I or pretreatment station II alone, and the combination of pretreatment stations I and II. Also, it should be understood that it is within this invention to reverse the sequence of pretreatment stations I and II.

Further, while the treatment and sealing dies are shown in FIG. 3 to be reciprocating, it should be understood that this invention includes like dies being mounted on cylinders. It is preferred that there be a firm back-up base for the treatment dies to press against for the pretreatment operation according to this invention.

The second layer of material 14 that is to be bonded to the first layer 12 is guided into position from roll 24 by a pair of guide rolls 38 in order that it can be positioned in juxtaposition under sealing means 40 at sealing station III. Sealing station III shows sealing means 40 comprising base 46 having attached to it frame 42 with drive mechanism 43 and platen 44 holding sealing die 45. Again, while sealing die, as shown in FIG. 3, is reciprocating, it can also be rotary. It should be apparent that multiple stations for pretreatment and sealing may be used. The apparatus may be rotary or reciprocating or combinations thereof to allow the most practical equipment set-up. Sealing station III provides suitable heat and pressure to seal the desired areas of the sheets together under conventional conditions of heat sealing polymeric materials such as polyolefins. The sealing die at sealing station III may be smaller than the area of the spunbonded olefin so as to provide a non-sealed area around the edge of the spunbonded olefin sheet. When it is desired to seal to the edge of the spunbonded olefin sheet and equal pretreatment to the entire peel-seal area has been effected, the die may have a step-recess of about 0.002 to about 0.005 inch at the edge so that a weak seal is formed at the edges of the spunbonded olefin sheet.

Slitting station IV shows slitting means 50 comprising rollers 51 and 52 which longitudinally slits the moving web in the desired locations as shown in FIG. 2 at station IV. It is recognized that razors or any suitable slitting means can be used.

Draw rollers 48 and 49 draw the plastic webs through the machine with indexing controlled by electric eye or mechanical measuring. After passing through draw rollers 48 and 49 the plastic web passes through shearing station V having shearing means 55 comprising knife 56 and anvil 57. At shearing station V containers are cut transversly and may be collected by any suitable means such as conveyor 58. The finished pouches are shown in FIG. 2 at station VI corresponding to the conveyor means.

The process of this invention may comprise drawing a web of spunbonded olefin material to a pretreatment station. At the pretreatment station the spunbonded olefin sheet is treated in one or both of two pretreatment operations by subjecting the peel-seal area of the spunbonded olefin to heat and pressure for a time sufficient to render the peel-seal area susceptible to conventional heat sealing to a second polymeric thermoplastic sheet material. It will be obvious to one skilled in the art that the apparatus and methods shown in FIGS. 2 and 3 are merely exemplary of one method of making a particular pouch and that other methods and apparatus well known in the art may be utilized for fabrication of other shapes and configurations of containers. This invention relates to the process for forming the peelable seals regardless of configuration.

I have found that unexpectedly high temperatures are suitable for the pretreatment according to this invention. The temperature of the surface of the spunbonded polyolefin in the pretreatment areas is suitably as high as 330° F. during pretreatment according to this invention. Temperatures of about 255° to about 330° F. are suitable for the pretreatment, about 270° to about 330° F. being preferred. The upper level of pressure suitable for pretreatment according to this invention is governed by the machinery used. Pneumatic or hydraulic machinery readily affording 500 psig is suitable. Pressures of about 30 to about 500 psig are suitable, about 100 to about 300 psig being preferred. Dwell times for pretreatment of about 0.3 to about 2 seconds are suitable, about 0.3 to about 1.3 second being preferred. The temperature-time-pressure treatment parameters may be changed somewhat with differing thickness or densities of the spunbonded olefin sheet. These adjustments may be readily ascertained to achieve desired pretreatment. When the higher temperature is used the time and/or pressure components should be reduced and conversely when the temperatures are in the lower portion of the range, higher times and/or pressures are suitable. The temperature-pressure-time ranges are particularly suited for spunbonded polyolefin in the range of about 1.8 to 2.2 ounces per square yard.

One process of this invention especially suited for use with pneumatic or hydraulic machinery enabling use of higher temperatures and pressures than previously is to pretreat the peel-seal area of spunbonded olefin material at a surface temperature of 300° F. with a pressure of 170 psig for a dwell time of 0.8 second. When polyethylene sheet material is sealed by conventional heat-pressure sealing, a very satisfactory peel-seal is obtained. Very satisfactory peel-seals have also been obtained with the same type of materials at surface temperatures of 310° F., pressures of 250 psig with a dwell time of 0.5 second.

One pretreatment of this invention is with suitable pressure and heat to the whole area to be sealed. It has been found for pretreatment of spunbonded olefin sheets of about 0.008 inch thickness and density of about 2.2 ounces per 1000 square inches, that temperatures of about 265° to about 290°. are suitable for this pretreatment with a dwell time of about three-quarter to about two seconds at a pressure of about 40 to about 80 psig. It has been found especially suitable to use for the entire seal area pretreatment a temperature of about 280° F., dwell time about 1.8 seconds and pressure about 50 psig. The pretreatment as disclosed in this paragraph may be achieved in pretreatment station II shown in FIGS. 2 and 3.

Another pretreatment of this invention is with suitable pressure and heat to the areas of the spunbonded olefin which form the edges of the area of the peel-seal connection. It has been found for pretreatment of spunbonded olefin sheet of about 0.008 inch thickness and density of about 2.2 ounces per 1000 square inches that temperature of about 275° to about 300° F. are suitable for this pretreatment with a dwell time of about one-half to about 2 seconds at a pressure of about 60 to about 100 psig. It has been found especially suitable to use for the edge pretreatment a temperature of about 290° F., dwell time about 1.5 seconds and pressure about 70 psig. The pretreatment as disclosed in this paragraph may be achieved in pretreatment station I shown in FIGS. 2 and 3.

Containers produced according to this invention having the above pretreatments have shown an incidence of tearing of the spunbonded olefin visible to the naked eye of less than three percent. Previous to this invention, I have found uncoated spunbonded olefin sheets sealed to polyethylene produced tearing upon opening peel-seals with a frequency much higher than acceptable for medical containers.

It should be understood that, though the use of unsupported polyethylene film is described in the above specific examples as the material 14, that anything which can be heat sealed to spunbonded olefin, such as a coated polypropylene, can also be used as within the teachings of this invention.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A method for forming peelable seals between uncoated spunbonded olefin sheet material and a synthetic polymeric thermoplastic sheet material while maintaining a substantial portion of said spunbonded olefin sheet untreated and breathable comprising; modifying the surface of the spunbonded olefin sheet in the area of the desired peelable seal by pretreatment with heat and pressure to substantially reduce high spots and internal weaknesses to render the sealing area susceptible to having said synthetic polymeric thermoplastic material peelably joined thereto in said pretreated area by conventional heat-pressure sealing, and peelably sealing said pretreated spunbonded olefin sheet to said synthetic polymeric thermoplastic sheet material by conventional heat-pressure sealing only in said pretreated area, said heat pretreatment raising the temperature of said olefin sheet material adjacent a heating means to about 255° to about 330° F.

2. The method of claim 1 wherein said temperature is about 270° to about 330° F.

3. The method of claim 1 wherein said pressure is greater than 30 psig.

4. The method of claim 3 wherein said pressure is about 30 to 500 psig.

5. The method of claim 1 wherein said temperature is about 270° to about 330° F. and said pressure is about 100 to about 300 psig.

6. The method of claim 1 wherein said pretreatment is performed with a dwell time of about 0.3 to about 2 seconds.

7. The method of claim 1 wherein said temperature is about 270° to about 330° F., said pressure is about 100 to about 300 psig, and the pretreatment is performed with a dwell time of about 0.3 to about 1.3 second.

8. The method of claim 1 wherein higher conditions of temperature and pressure are applied to the edge of the peel-seal area than are applied to the entire peel-seal area.

9. The method of claim 1 wherein said seal stops at a distance inward from the edge of said spunbonded olefin sheet material.

10. The method of claim 1 wherein said seal is obtained by the sealing die having a recess from the surface at the outside edges so that a weak seal is obtained at the edge.

11. The method of claim 1 wherein said synthetic polymeric thermoplastic material is selected from the group consisting of polyethylene, a laminate having polyethylene as a surface and a coated or laminated material having a heat sealable surface coating.

12. The method of claim 1 wherein said synthetic polymeric thermoplastic material is sheet polyethylene.

13. The method of claim 1 wherein the product to be packaged is placed within the pretreated area and said sealing of said pretreated spunbonded olefin to said synthetic polymeric thermoplastic material by conventional heat-pressure sealing seals said product within a peel-seal container.

14. The method of claim 1 wherein said pretreatment is performed to three edges of the spunbonded olefin sheet, the fourth edge remaining untreated.

* * * * *